United States Patent
Ikeda et al.

(10) Patent No.: US 6,235,490 B1
(45) Date of Patent: *May 22, 2001

(54) IMMUNOASSAY OF HUMAN GROWTH HORMONE WITH A MOLECULAR WEIGHT OF ABOUT 20,000

(75) Inventors: Ichiro Ikeda; Naoko Kono; Tadashi Makino; Yoshihide Hashimoto, all of Chiba (JP)

(73) Assignee: Mitsui Chemicals, Inc. (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/181,854

(22) Filed: Oct. 29, 1998

Related U.S. Application Data

(62) Division of application No. 08/876,042, filed on Jun. 13, 1997.

(30) Foreign Application Priority Data

Jun. 18, 1996 (JP) ..................................................... 8-156948

(51) Int. Cl.$^7$ ........................ G01N 33/577; G01N 33/74; C12N 5/20; C07K 14/61
(52) U.S. Cl. ......................... 435/7.94; 435/7.1; 435/336; 530/388.24
(58) Field of Search .................................... 435/7.94, 7.1, 435/336; 530/388.24

(56) References Cited

U.S. PATENT DOCUMENTS 5,945,296 * 8/1999 Hansson et al. .................... 435/7.93

FOREIGN PATENT DOCUMENTS 63-273496 * 10/1988 (JP) .

OTHER PUBLICATIONS

Mazza et al. Relationship between the antigenic topography and the structure of human growth hormone. Endocrinology, (1990 Sep.) 127 (3) 1002–8.*

Ivanyi J. Study of antigenic structure and inhibition of activity of human growth hormone and chorionic somatomammotropin by monoclonal antibodies. Mol. Immunol, (Dec. 19, 1982) (12) 1611–8.*

Celniker et al. Variability in the quantitation of circulating growth hormone using commercial immunoassays. J. Clin. Endocrinol. Metab. (1989), 68(2), 469–76.*

Lewis et al. Variant forms and fragments of human growth hormone in serum. Acta Paediatr Suppl Apr. 1994;399:29–31; discussion 32.*

Mellado et al. Characterization of monoclonal antibodies specific for the human growth hormone 22K and 20K isoforms. J. Clin. Endocrinol. Metabl, (Apr. 1996) 81 (4) 1613–8.*

Lewis et al. Biologic properties of the 20k–dalton variant of human growth–hormone: A review. Endocrinologia Japonica, 1987, vol. 34, pp. 73–85.*

Woodhead et al. Accuracy of growth hormone measurements. Horm. Res., (1991) 36 Suppl 1, 17–20.*

Harlow et al. Antibodies: A laboratory manual. Cold Spring Harbor, NY, Publisher: Cold Spring Harbor Laboratory, 1988.*

Clark et al. Enzyme–linked immunosorbent assay (ELISA): Theoretical and practical aspects, In, Enzyme–immunoassay, Boca Raton, Fla., CRC Press, 1987, Ed., Maggio, Edward T.

Hashida et al. Human growth hormone (hGH) in urine and its correlation to serum hGH examined by a highly sensitive sandwich enzyme immunoassay. Clin. Chim. Acta., (Jan. 30, 1987) 162 (2) 229–35.

Dore et al. Contribution of hGH20K variant to blood hGH response in sauna and exercise. Eur. J. Appl. Physiol., (1991) 62 (2) 130–4.

* cited by examiner

Primary Examiner—David S. Romeo
(74) Attorney, Agent, or Firm—Burns, Doane, Swecker & Mathis, L.L.P.

(57) ABSTRACT

An animal cell capable of producing an antibody specific to a human growth hormone having a molecular weight of 20,000 (20 k hGH) was prepared from an animal immunized with 20 k hGH. The animal cell was fused with a myeloma cell to produce a monoclonal antibody which specifically reacted to 20 k hGH, but substantially not to 22 k hGH. The monoclonal antibody was useful for immunoassay of 20 k hGH.

10 Claims, 1 Drawing Sheet

IMMUNOASSAY OF HUMAN GROWTH HORMONE WITH A MOLECULAR WEIGHT OF ABOUT 20,000

This application is a divisional of application Ser. No. 08/876,042, filed Jun. 13, 1997, the contents of which are incorporated herein by reference.

A monoclonal antibody specifically reactive to a human growth hormone with a molecular weight of about 20,000, a cell line capable of producing the monoclonal antibody and an immunoassay of a human growth hormone having a molecular weight of about 20,000 using the monoclonal antibody.

BACKGROUND OF THE INVENTION

1. Field of the Invention

This invention relates to a monoclonal antibody utilized in an assay of a human growth hormone with a molecular weight of about 20,000; a cell line capable of producing the monoclonal antibody; and a sensitive immunoassay of a human growth hormone with a molecular weight of about 20,000 by means of the monoclonal antibody.

2. Description of the Related Art

It is known that in a human body, there are two ma in human growth hormones (sometimes referred to as "hGH"); peptide hormones with a molecular weight of about 22,000 (referred to as "22 k hGH") and about 20,000 (referred to as "20 k hGH"). 22 khGH is a protein with 191 amino acids, while 20 k hGH is a protein with 176 amino acids.

Both 20 k hGH and 22 k hGH are proteins originally encoded in a single gene, and are, therefore, very similar in their amino acid sequences, except for a difference that 20 k hGH has a structure with a deletion of 15 amino acids of $32^{nd}$ to $46^{th}$ from the N-terminus of 22 k hGH.

It is known that in an adult with normal secretion, a hGH level is below about 5 ng/mL as a baseline level in the morning.

The previous studies have shown that in a human body 22 k hGH exists much more than 20 k hGH; specifically 20 k hGH could account for 5 to 20% of the total hGHs.

The blood level of the hGHs varies constantly and largely, i.e., significantly varies within a day and increases during exercise or sleeping. However, the above findings for the quantitative ratio between 20 k hGH and 22 k hGH have been obtained by measuring hGHs extracted from a human pituitary. Therefore, the quantitative ratio between them in their natural secretion dynamics in a human body is still unknown and whether it varies in a short time is also unknown.

As a drug, 22 k hGH has been marketed, and has been studied more intensively than 20 k hGH.

The biological activities of 20 k hGH have been recently reported; its growth-promoting activity is comparable to that of 22 k hGH, is less inducible in an abnormal glucose tolerance and could be less diabetogenous (Lewis, U. J., et al., Endocriniol. Japon, 34, 73–85(1987)). This suggests that when a human growth hormone is used as a drug 20 k hGH could have less risk of adverse drug reactions than 22 k hGH. Thus, usefulness of 20 k hGH has been increasingly paid much attention as a drug for a substitution therapy to an adult with growth hormone deficiency (Hisao Seno, Igaku No Ayumi, 165, 247–251(1993)).

However, there had been no successful cases for producing a large amount of pure 20 k hGH before the present inventors have first established a preparation process recently, and thus there has not been obtained 20 k hGH with sufficient amount and purity to conduct a variety of studies.

Therefore, 20 k hGH has never been clinically applied. In addition, since there have been not developed a sensitive immunoassay for 20 k hGH, it has been difficult for a long time to determine relationship between the activities and the molecular structures of 20 k hGH and 22 k hGH. The previous studies for 20 k hGH have been mainly in a molecular or cellular level using a small amount of 20 k hGH extracted from a living body, and there have been no clinical studies for 20 k hGH.

The determination methods of hGHs will be described. There are several known determination methods for hGHs in human blood or urine to explicate biological roles of hGHs (e.g., Hashida and Ishikawa et al., Clinica. Chimica. Acta, 162, 229–235(1987)).

It is essential for developing hGHs as a drug that an accurate secretion dyanamics is determined in a clinical trial, including a baseline blood level of hGHs in a human body. In addition, the determination method is required to be sensitive with no errors.

Since 22 k hGH has been clinically applied, there are immunoassays capable of determining a baseline blood level in the morning for 22 k hGH (below 5 ng/mL).

For example, for 22 k hGH, an immunoassy using an antibody specific to 22 k hGH has been disclosed in Japanese Patent Laid-Open No. 273496/88 (JP-A 63-273496). The specification describes that its cross-reactivity to 20 k hGH is 15% However, since the purity level of the standard 20 k hGH used in the method is not described, the above percentage may be quite questionable.

On the other hand, all of the previous examples for immunoassays for 20 k hGH were to measure around a higher value (1 ng/mL) of 20 k hGH secretion under exercise load. Any of the previous determination methods has a performance only for investigating human 20 k hGH in cellular level due to its inadequate cross-reactivity and sensitivity, i.e., does not have an adequate sensitivity to determine its baseline blood level.

The known immunoassays for 20 k hGH are as follows.

There is an assay wherein a value for 20 k hGH is obtained by subtracting a measured value for an antibody specifically reacting with 22 k hGH from a measured value for an antibody reacting with all hGHs (Eur. J.Appl.Physiol., 62, 130–134(1991)). The author has assumed that hGHs other than 22 k hGH would consist of 20 k hGH. Recently, several variants of hGH have been discovered, which will react with an antibody as total hGHs like 20 k hGH. Therefore, the author would probably have determined the variants as 20 k hGH, and thus the measured values for 20 k hGH must be quite inaccurate.

A monoclonal antibody specific to 20 k hGH has been disclosed by Mario Mellado, et al. (Journal of Clinica Endocrinology and Metabolism, 81, 1613–1618(1996)), who describes that cross-reactivity to 22 k hGH is below 1%, and does not demonstrate an actual example of determination of 20 k hGH in human body fluid. As discussed later, it is impossible in theory to elucidate the secretion dynamics in a human body of 20 k hGH using the monoclonal antibody of this article.

Hence, there have been no sensitive immunoassays capable of evaluating the secretion dynamics of 20 k hGH. Determining the secretion dynamics of 20 k hGH means that 20 k hGH can be accurately determined in a relatively low level near its baseline blood level. For an immunoassay of 22 k hGH, the situation is similar in terms of accurate determination in relatively lower level around its baseline blood level. For 20 k hGH, there are, however, intrinsic problems in cross-reactivity and sensitivity, but not for 22 k hGH. Thus, it has been difficult to provide a sensitive immunoassay for 20 k hGH in contrast to the immunoassays for 22 k hGH.

Cross-reactivity is a phenomenon observed when an epitope reactive to an antibody is also reactive to another antibody. The cross-reactivity should be taken into consideration in an immunoassay for 22 k hGH. However, it will not be a significant problem because of the following reasons: First, 22 k hGH is contained in blood much more than 20 k hGH (5 to 20 times). Next, as described above, 22 k hGH has a unique sequence consisting of 15 amino acids. Therefore, if a monoclonal antibody capable of recognizing the unique sequence as an epitope could be prepared, a monoclonal antibody which may specifically react with 22 k hGH and be adequately sensitive would be readily prepared.

On the other hand, for an immunoassay for 20 k hGH, it is difficult to solve the problems of cross-reactivity and sensitivity due to the following reasons.

First, 20 k hGH is much less than 22 k hGH in blood (1/5 to 1/20). This simply means that a sensitive immunoassay for 20 k hGH is required to has a sensitivity 10 times higher than a sensitive immunoassay for 22 k hGH. Furthermore, cross-reactivity to 22 k hGH significantly affects the precision in the measurement.

Next, 20 k hGH is different from 22 k hGH in that it does not have a unique amino acid sequence. If anything, the ligation segment between the termini of the deletion of the 15 amino acids from 22 k hGH, i.e., the sequence wherein $31^{st}$ phenylalanine and $32^{nd}$ asparagine ($47^{th}$ amino acid from N-terminus in 22 k hGH) from N-terminus are adjacent to each other, might be considered to be a unique amino acid sequence in 20 k hGH. Lewis et al have immunized an animal with a polypeptide coupled with albumin containing a region in the vicinity of the amino acid sequence (an amino acid sequence of $28^{th}$ to $38^{th}$ from N-terminus of 20 k hGH) and attempted to prepare a monoclonal antibody recognizing the polypeptide as an epitope, but have been unsuccessful (Lewis U. J. et al, Endocrinol Japon, Vol.34, pp.73–85 (1987)).

Thirdly, to prepare a monoclonal antibody which is little cross-reactive to 22 k hGH, but is adequately sensitive, it is necessary to separate a number of cells producing a monoclonal antibody, from which the cells producing the desired monoclonal antibody are then selected. Furthermore, in this case, the animals for preparing the antibody-producing cells should be adequately immunized, requiring a large amount of pure 20 k hGH.

To date 20 k hGH has not been commercially available and there are few methods for its preparation. In such a situation, it is difficult to obtain 20 k hGH in an amount to adequately immunize an animal. Before this invention, it has been difficult to adequately immunize an animal with 20 k hGH for preparing antibody-producing cells. Consequently, it has been quite difficult to obtain cells producing the desired monoclonal antibody.

Thus, in contrast to a monoclonal antibody specific to 22 k hGH, it has been hard to obtain a monoclonal antibody specific to 20 k hGH, and therefore, it has been difficult to establish a sensitive immunoassay for 20 k hGH using the monoclonal antibody.

The followings will describe the problems of cross-reactivity and sensitivity in a sensitive immunoassay for 20 k hGH in terms of the above process described by Mellado et al.

Mellado et al. describe that the monoclonal antibody reactive to 20 k hGH has below 1% of cross-reactivity to 22 k hGH. If a sample containing 5 ng/mL of 22 k hGH and 250 pg/mL of 20 k hGH is subject to an immunoassay using a monoclonal antibody with 1% of cross-reactivity, a measured value will be 5000 pg/mL×0.01+250 pg/mL=300 pg/mL, giving an error of 20% compared with the true value, which indicates that determination of a baseline blood level is not feasible.

In addition, Mellado et al. describe that the measuring sensitivity of the immunoassay is 4 ng/mL. Since a peak level of 20 k hGH in human blood is about 1 ng/mL for a normal adult, the immunoassay described by Mellado et al. can never determine the baseline blood level of 20 k hGH. In other words, this method can never elucidate the secretion dynamics of 20 k hGH in human blood.

As described above, Mellado et al. have not solved the above problems of cross-reactivity and sensitivity in an immunoassay for 20 k hGH. That is, the monoclonal antibody described by Mellado et al. and the immunoassay therewith cannot be applied to a clinical study for development of 20 k hGH as a drug.

SUMMARY OF THE INVENTION

To solve the problems, this invention should provide a sensitive immunoassay for 20 k hGH which is useful in development of 20 k hGH as a drug, can determine the baseline blood level of 20 k hGH, and can allow us to elucidate the secretion dynamics of 20 k hGH.

Thus, an objective of this invention is to provide a monoclonal antibody which is specifically reactive to 20 k hGH, but substantially unreactive to 22 k hGH and its preparation process; a cell line capable of producing the antibody; and an immunoassay for 20 k hGH using the antibody which can accurately and directly quantify 20 k hGH in human blood.

The inventors have attempted to prepare the desired monoclonal antibody, improving the followings to solve the above problems.

First, a large amount of pure 20 k hGH was prepared, and it was repeatedly administered to an animal for adequate immunization. Next, as a screening procedure we used a sandwich immunoassay in a liquid system instead of a previous immunoassay in a solid system. Because of these improvements, we have been successful in preparing a monoclonal antibody which is specifically reactive to 20 k hGH, but substantially unreactive to 22 k hGH. Furthermore, we have established a sensitive immunoassay which can sepcifically determine 20 k hGH in a level around its baseline blood level using the monoclonal antibody, to achieve this invention.

This invention provides a monoclonal antibody which is specifically reactive to 20 k hGH, but substantially unreactive to 22 k hGH; a cell line producing the monoclonal antibody; and an immunoassay for 20 k hGH using the monoclonal antibody.

This invention provides a cell line producing a monoclonal antibody which is specifically reactive to 20 k hGH, but substantially unreactive to 22 k hGH. This invention also provides a monoclonal antibody which is specifically reactive to 20 k hGH, but substantially unreactive to 22 k hGH, and a process for preparation of the monoclonal antibody. Furthermore, this invention provides an immunoassay using the monoclonal antibody of this invention.

The monoclonal antibody of this invention has a markedly lower cross-reactivity to 22 k hGH and a high affinity to 20 k hGH than those of the prior art. The immunoassay using the monoclonal antibody of this invention may be, therefore, an effective means for elucidating the secretion dynamics of 20 k hGH, by permitting determination of the baseline blood level of 20 k hGH which has not been feasible. Since 20 k hGH would be useful as a drug such as a remedy for growth impairment, the immunoassay of this invention is useful for developing 20 k hGH as a drug.

DETAILED DESCRIPTION OF THE INVENTION AND PREFERRED EMBODIMENTS

Figure 1:
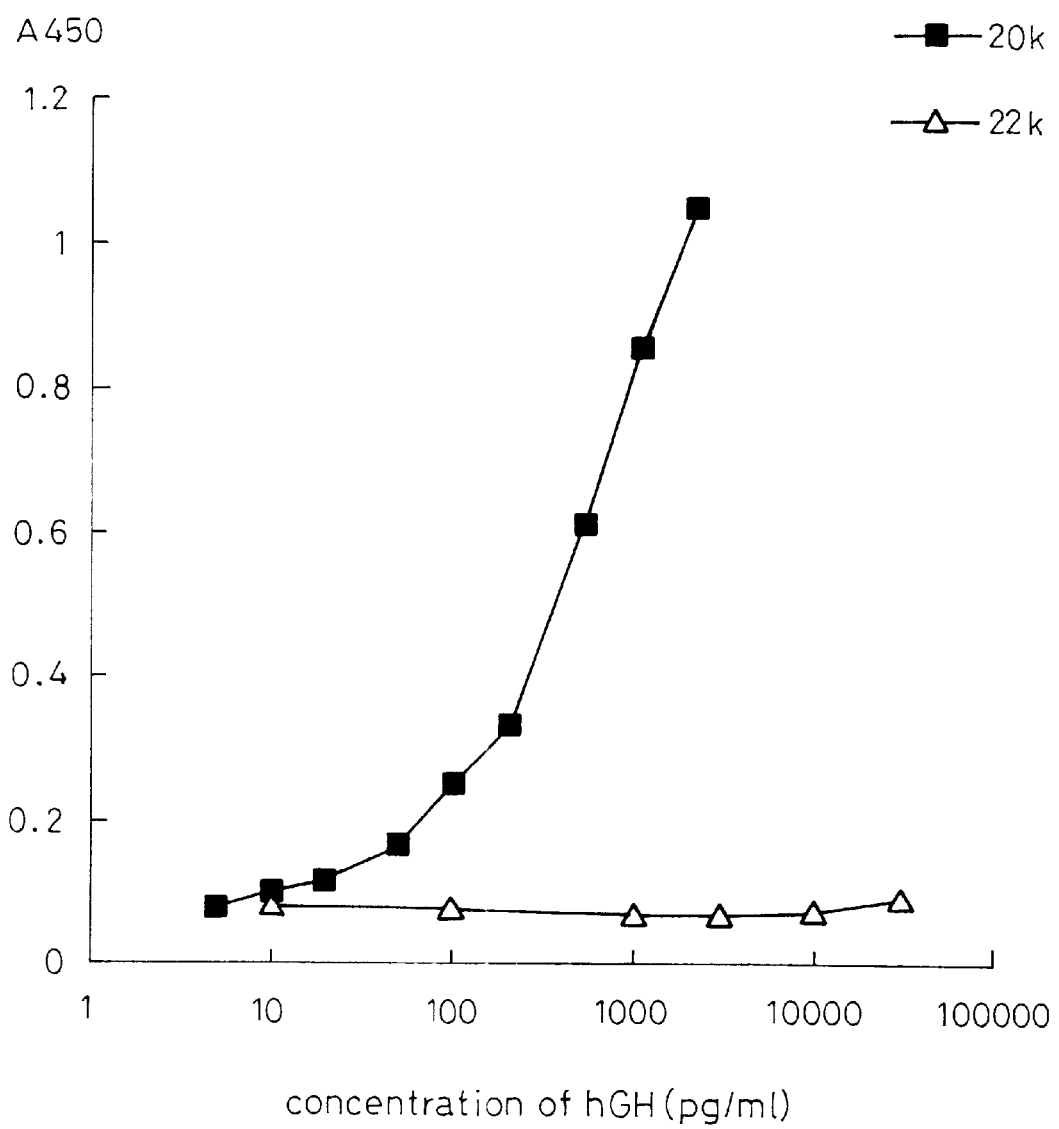
FIG. 1 shows reactivity of 20 k hGH and 22 k hGH to the MTC6A monoclonal antibody in a sandwich immunoassay.

This invention will be described in detail.

The hormone 20 k hGH with which the monocloal antibody of this invention reacts, is a protein comprising 176 amino acids, including those derived from human pituitary and human blood; and those which are produced by a gene recombination technique. There are two types of known 20 k hGH in which the $14^{th}$ amino acid from N-terminus is serine or methionine, and both of which may be used in this invention.

The hormone 22 k hGH with which the monoclonal antibody of this invention does not react, is a protein comprising 191 amino acids, including those derived from human pituitary and human blood; and those produced by a gene recombination technique.

The monoclonal antibody of this invention is one which is specifically reactive to 20 k hGH, but substantially unreactive to 22 k hGH.

For the purpose of this invention, a monoclonal antibody which is specifically reactive to 20 k hGH, but substantially unreactive to 22 k hGH is one which has an extremely low cross-reactivity to 22 k hGH and causes a negligible error due to its reactivity to 22 k hGH, in determining 20 k hGH, e.g., one whose cross-reactivity is below 0.1%, preferably below 0.03%, in a sandwich immunoassay illustrated later.

The globulin type of the monoclonal antibody of this invention is not restricted as long as it is specifically reactive to 20 k hGH, but substantially unreactive to 22 k hGH; for example, IgG, IgM, IgA, IgE and IgD.

The monoclonal antibody of this invention may be prepared from a cell line producing the antibody.

The cell line producing the monoclonal antibody of this invention is not restricted as long as it can produce a monoclonal antibody which is specifically reactive to 20 k hGH, but substantially unreactive to 22 k hGH, and, for example, may be obtained as a hybridoma via a cell fusion of a cell producing an anti-20 k hGH antibody with a myeloma cell strain. Such a hybridoma includes MTC6A strain (FERM BP-5913).

Specifically, a hybridoma cell strain producing a monoclonal antibody which is specifically reactive to 20 k hGH, but substantially unreactive to 22 k hGH, may be prepared by the following cell fusion technique.

Antibody-producing cells which may be used in a process for preparing the cell strain of this invention, includes spleen cells, lymphatic node cells and B-lymphocytes. Antigens which may be used include 20 k hGH extracted from a pituitary or produced by a gene recombination technique. An immunized animal may be a mammal such as a mouse and a rat. An antigen may be administered to the animal as usual.

For example, a suspension or emulsion is prepared with an adjuvant such as complete Freund's adjuvant and incomplete Freund's adjuvant and 20 k hGH as an antigen, and is administered several times to an animal, for example, intravenously, subcutaneously, intracutaneously or intraperitoneally, for immunization. From the immunized animal, antibody-producing cells such as spleen cells are removed, which are then fused with myeloma cells according to a known procedure (G. Kohler et al., Nature, 256, 495(1975)) to provide the hybridoma cells of this invention.

For a mouse, a myeloma cell strain which may be used in the cell fusion includes P3×63Ag8, P3U1 and Sp2/0 strains. A fusion accelerator such as polyethylene glycol and Sendai virus may be used in the cell fusion, and the hypoxanthine-aminopterin-thymidine (HAT) medium may be used as usual for selection of a hybridoma after the cell fusion.

The hybridoma prepared by the cell fusion is cloned by, for example, a limiting dilution, which is then screened by an immunoassay with 20 k hGH and 22 k hGH (e.g., Jenotropine™ (Sumitomo Pharm.)) to provide a cell line producing a monoclonal antibody which is specifically reactive to 20 k hGH, but substantially unreactive to 22 k hGH.

The cell strain of this invention is screened by (1) coupling an antibody specifically reactive to a human growth hormone (referred to as "anti-hGH antibody") to an insoluble carrier to form an hGH-antibody-coupled insoluble carrier, (2) reacting the hGH-antibody-coupled insoluble carrier with 20 k hGH to form an anti-hGH antibody—20 k hGH coupling product, (3) reacting the coupling product to the monoclonal antibody in the medium of the above hybridoma to form a complex of anti-hGH antibody—20 k hGH—20 k hGH monoclonal antibody, (4) coupling the complex to an enzyme-labeled antibody to form a complex of anti-hGH antibody—20 k hGH—20 k hGH monoclonal antibody—enzyme-labeled antibody, and (5) determining the activity of the enzyme labeling the antibody using the above complex with the enzyme-labeled antibody to select hybridoma cells.

A screening by an immunoassay will be described in detail.

In the first step, an anti-hGH antibody is coupled to an insoluble carrier to form an anti-hGH-antibody-coupled insoluble carrier. The insoluble carrier may include a microplate, plastic beads, glass beads and magnetic fine particles. The anti-hGH antibody is one reactive to both 20 k hGH and 22 k hGH, and may be either monoclonal or polyclonal. It may be preferably an anti-hGH rabbit polyclonal antibody purified by affinity chromatography, specifically F(ab')2 fragment or Fab' fragment to reduce non-specific adsorption. The antibody may be coupled to these insoluble carriers by a known chemical coupling process, but may be adequately coupled by a physical adsorption. Specifically, the anti-hGH antibody is dissolved in carbonate or phosphate buffer, the above insoluble carrier is added to the solution, the mixture is left at 0° C. to room temperature for at least one hour, and then the mixture is washed with buffer such as Tris-HCl buffer or phosphate buffer containing Tween 20 (polyoxyethylene-sorbital-monolaurate) and sodium azide, to remove uncoupled antibody.

In the second step, the anti-hGH-antibody-coupled insluble carrier prepared in the first step is reacted with an appropriate amount of 20 k hGH, to form an anti-hGH antibody—20 k hGH coupling product in which 20 k hGH is specifically coupled to the abtibody-coupled insoluble carrier.

In the third step, the culture medium of the hybridoma according to the above process is added to the coupling product prepared in the above second step to react with the monoclonal antibody in the medium to provide a sandwich complex of anti-hGH antibody—20 k hGH—anti-20 k hGH monoclonal antibody on the anti-hGH-antibody-coupled insoluble carrier.

In the fourth step, the sandwich complex prepared in the above third step is reacted with an enzyme-labeled antibody to an antibody of an immunized animal (referred to as "an enzyme-labeled antibody"), to determine the amount of the anti-20 k hGH monoclonal antibody in the sandwich complex. The antibody to the antibody of the immunized animal used in the immunoassay may be either monoclonal or polyclonal, particularly a polyclonal antibody purified by affinity chromatography. The labeling enzyme includes horse radish peroxidase, alkaline phosphatase, glucose oxidase and β-galactosidase. The antibody to the antibody of the immunized animal may be labeled with any of these enzymes by a well-known procedure such as oxidizing a sugar chain of an enzyme with periodic acid to form an aldehyde group to which, for example, an amino acid of an anti-hGH antibody is then coupled; introducing an appropriate group such as maleimide group and pyridylsulfide group into the enzyme and coupling the introduced group to a thiol group in Fab' fragment of the anti-hGH antibody.

In the fifth step, the sandwich complex prepared in the fourth step to which the enzyme labeled antibody is coupled, is quantified for its enzyme activity.

The enzyme activity depends on the amount of the monoclonal antibody in the culture medium of the hybridoma reactive to 20 k hGH. The activity may be determined by adding a substance as a substrate for the enzyme.

The screening in the above immunoassay may be, of course, the following procedure; coupling the antibody to the antibody of the immunized animal to the insoluble carrier to form an insoluble carrier coupled to the antibody to the antibody of the immunized animal, reacting the coupling product with the monoclonal antibody in the medium of the hybridoma and then with an appropriate amount of 20 k hGH, and detecting 20 k hGH having reacted with the monoclonal antibody in the medium of the hybridoma using an immunoassay to select hybridoma cells producing an antibody strongly reactive to 20 k hGH, which may be within this invention because of having an effect comparable to the screening procedure using the above immunoassay.

The desired monoclonal antibody of this invention may be prepared with the hybridoma cells thus obtained, by culturing the hybridoma cells via a usual cell culture or an ascites formation technique, and purifying the monoclonal antibody from the resulting culture supernatant or ascites.

The monoclonal antibody from the culture supernatant or the ascites may be purified as usual; for example, ammonium sulfate fractionation, gel filtration, ion-exchange chromatography, affinity chromatography or any combination thereof, as appropriate.

An immunoassay for 20 k hGH of this invention using a monoclonal antibody utilizes the monoclonal antibody; for example, enzyme immunoassay, radioimmunoassay, fluorescence immunoassay and luminescence immunoassay, preferably enzyme immunoassay. The enzyme immunoassay may be preferably so-called sandwich immunoassay wherein the monoclonal antibody is coupled to an insoluble carrier to form a monoclonal-antibody-coupled insoluble carrier, which is used in the assay.

The determination process of this invention will be illustrated, based on sandwich immunoassay.

In the step (1), the monoclonal antibody of this invention is coupled to an insoluble carrier to form a monoclonoal-antibody-coupled insoluble carrier, which is then reacted with a test solution containing a human growth hormone to form a coupling product in which only 20 k hGH is specifically coupled with the monoclonal-antibody-coupled insoluble carrier. The insoluble carrier may include a microplate, plastic beads, glass beads and magnetic fine particles. The monoclonal antibody may be coupled to these insoluble carriers by a known chemical coupling process, but may be adequately coupled by a physical adsorption. Specifically, the monoclonal antibody of this invention is dissolved in buffer such as carbonate buffer and phosphate buffer, the above insoluble carrier is added, the mixture is left at 0° C. to room temperature for at least one hour, and then the mixture is washed with buffer such as Tris-HCl buffer and phosphate buffer containing Tween 20 (polyoxyethylene-sorbital-monolaurate) and sodium azide, to remove uncoupled antibody. Next, the resulting monoclonal-antibody-coupled insoluble carrier is reacted with a test solution containing a human growth hormone to be coupled to the 20 k hGH in the test solution.

In the step (2), the coupling product prepared in the step (1) is reacted with an enzyme-labeled anti-hGH antibody (referred to as "an anti-hGH enzyme-labeled antibody"), to form a sandwich complex of anti-20 k hGH monoclonal antibody of this invention—20 k hGH—anti-hGH enzyme-labeled antibody on the monoclonal antibody-coupled insoluble carrier.

The anti-hGH antibody used in the anti-hGH enzyme-labeled antibody may be either an antibody which is reactive only to 20 k hGH and recognizes an epitope which is not recognized by the above 20 k hGH monoclonal antibody, or an antibody reactive to both 20 k hGH and 22 k hGH, as well as may be either monoclonal or polyclonal. In particular, a preferred anti-hGH antibody may be an anti-hGH rabbit polyclonal antibody purified by affinity chromatography; specifically F(ab')2 fragment and Fab' fragment is desirable.

The labeling enzyme includes horse radish peroxidase, alkaline phosphatase, glucose oxidase and β-galactosidase.

The anti-hGH antibody or F(ab')2 fragment or Fab' fragment of the antibody may be labeled with any of these enzymes by a well-known procedure such as oxidizing a sugar chain of an enzyme with periodic acid to form an aldehyde group to which an amino acid such as an anti-hGH antibody is then coupled; introducing an appropriate group such as maleimide group and pyridylsulfide group into the enzyme and coupling the introduced group to a thiol group in Fab' fragment of the anti-hGH antibody.

In the step (3), the sandwich complex prepared in the step (2) is quantified for its enzyme activity. Since the enzyme activity depends on the amount of 20 k hGH which has been originally reacted, only 20 k hGH in the test solution may be quantified. The activity of the enzyme may be determined by adding a substance as a substrate for the enzyme. The activity may be also determined by using an anti-hGH biotin-labeled antibody instead of the anti-hGH enzyme-labeled antibody to form the sandwich complex of anti-20 k hGH monoclonal antibody of this invention—20 k hGH—anti-hGH biotin-labeled antibody on the monoclonal-antibody-coupled insoluble carrier, reacting the complex with an enzyme-labeled avidin or an enzyme-labeled streptoavidin to form a sandwich complex of anti-20 k hGH monoclonal antibody of this invention—20 k hGH—anti-hGH biotin-labeled antibody—enzyme-labeled avidin or enzyme-labeled streptoavidin, and then determining the enzyme activity in the sandwich complex.

In the above sandwich immunoassay, the activity may be, of course, determined, replacing the order of the anti-20 k hGH monoclonal antibody of this invention and the anti-hGH enzyme-labeled antibody. Since such a procedure has an effect comparable to the above sandwich immunoassay, it may be within this invention.

Samples as a control for determination in the immunoassay of this invention may include human blood, human urine and these which have been subject to treatment such as dilution, purification and pH adjustment.

Standard 20 k hGH used for developing a calibration curve for the immunoassay of this invention may be 20 k hGH prepared by a gene recombination technique.

The above immunoassay of this invention can specifically determine 20 k hGH. The immunoassay of this invention is extremely sensitive with the maximum measurement sensitivity of 0.001 ng/mL. Thus, the immunoassay of this invention can directly and accurately quantify only 20 k hGH around the range of its human baseline blood level.

EXAMPLES

This invention will be specifically illustrated, but not limited to, by the following examples.

Example 1
Preparation of an anti-20 k hGH monoclonal antibody (1) Immunization A Balb/c mouse (5 weeks old, female) was immunized five times in total with purified 20 k hGH prepared by gene recombination (JP-A 6-269292) as an antigen. In the first immunization, 100 µg of 20 k hGH mixed with complete Freund's adjuvant (Difco) was intraperitoneally administered. Then, 50 µg of 20 k hGH mixed with incomlete Freund's adjuvant (Difco) was administered three times, at intervals of two weeks. In the final immunization, two weeks after the $4^{th}$ immunization a solution of 50 µg of 20 k hGH in saline was injected in the caudal vein, and after additional three days spleen cells of the immunized mouse were used in cell fusion.

(2) Preparation of antibody-producing hybridoma cells by cell fusion

The spleen cells of the immunized were mixed with murine myeloma cells P3X63Ag8 in the proportion of about 5:1 to 10:1, and then the cells were fused as usual, using 50% (w/v) polyethylene glycol solution (GIBCO, average molecular weight: 4000) as a fusion accelerator. The fused cells were suspended in a culture medium consisting of IMDM medium containing 20% fetal bovine serum (GIBCO) with hypoxanthine, aminopterin and thymidine (HAT medium), in a level of $1 \times 10^6$ cells/mL as spleen cells. Aliquots (0.1 mL) of the suspension were poured to a 96-well microplate (Corning). The fused cells were cultured in a $CO_2$-incubator (37° C., 5% $CO_2$), while a half of the medium was replaced at intervals of 3–5 days. Hybridoma cells which could multiple in the HAT medium were selectively cultured.

(3) Screening

The wells in which colonization was observed were screened by an immunoassay to determine whether they contained an antibody to 20 k hGH in their supernatant. To a 96-well microplate (Greiner) were poured aliquots (50 µL) of an anti-hGH rabbit polyclonal antibody (10 µg/mL) in 0.1 M carbonate buffer, and then left overnight at 4° C. to be fixed. This plate was washed with washings (10 mM Tris-HCl buffer (pH: 8.0) containing 0.02% sodium azide and 0.05% Tween 20), to which were then added aliquots (100 µL) of blocking solution 1 (PBS containing 0.5% bovine serum albumin) for blocking. After blocking solution 1 was removed, to 48 of 96 wells and the other 48 wells were added aliquots (50 µL) of 20 k hGH (10 ng/mL) in blocking solution 1 and aliquots (50 µL) of 22 k hGH (trade name: Genotropin; Sumitomo Pharm.)(10 ng/mL) in blocking solution 1, respectively, and then shaken at room temperature for 2 hours. After washing the plate with washings, aliquots (50 µL) of the supernatant of the wells in the above (2) in which colonization was observed, were added to the 20 k hGH wells and the 22 k hGH wells, and then shaken at room temperature for 2 hours. After washing, to the wells were added aliquots (100 µL) of an alkaline phosphatase-labeled anti-murine Igs antibody (DAKO) 500-fold diluted by blocking solution 1, and then shaken at room temperature for 2 hours. After washing with washings, to the wells were added aliquots (50 µL) of a substrate solution (9.6% diethanolamine buffer (pH 9.6) containing 0.6% p-nitrophenyl phosphate and 0.5 mM magnesium chloride), and then shaken at room temperature for 30 min. To the reaction solutions, aliquots (50 µL) of 3N sodium hydroxide were added to quench the reaction, and absorbance at 405 nm was determined with Immunoreader (Nippon Intermed) to select colonies reacting more strongly with 20 k hGH than with 22 k hGH, for cloning.

(4) Cloning of the hybridoma

The hybridoma cells producing an antibody which reacts stronger with 20 k hGH than with 22 k hGH, were cloned three times by a limiting dilution, to provide a hybridoma MTC6A strain, producing an antibody which is specifically reactive to 20 k hGH, but substantially unreactive to 22 k hGH. MTC6A strain has been deposited, on May 30, 1996, with a deposit number FERM BP-5913 to the National Institute of Bioscience and Human-Technology of the Agency of Industrial Science and Technology of the Ministry of International Trade-and Industry, 1-1-1,Higashi, Tsukuba, Ibaragi, Japan, under the Budapest Treaty for Deposit of Microorganisms.

(5) Determination of the subclass of the monoclonal antibody produced by the hybridoma The subclass of the anti-20 k hGH monoclonal antibody produced by the obtained hybridoma MTC6A strain, was determined with a test paper for isotyping a murine monoclonal antibody (ISO Strip; Berlinger Mannheim). The subclass of the anti-20 k hGH monoclonal antibody produced by MTC6A strain was IgGI for a heavy chain and K for a light chain.

(6) Preparation of a monoclonal antibody

MTC6A strain was cultured and multiplied, and $1 \times 10^7$ cells were intraperitoneally inoculated into a Balb/c mouse having treated with Pristan before 2 weeks. After 10 to 14 days, ascites was taken from the abdomen of the mouse. The collected ascites was purified by affinity chromatography using Protein A (BIO RAD) to provide a MTC6A monoclonal antibody, the 20 k hGH monoclonal antibody of this invention.

Referential Example 1
Preparation of an anti-hGH rabbit polyclonal antibody and an anti-hGH labeled antibody (1) Immunization First, 100 µg of purified 20 k hGH prepared by gene recombination (JP-A 6-269292) was mixed with complete Freund's adjuvant (Difco) and the mixture was administered to a rabbit at several points of its back for immunization. Then, the animal was repeatedly immunized 5 times in total at intervals of 2 weeks, in a similar manner.

(2) Purification of the antiserum

The rabbit antiserum obtained from rabbit immunized in the above (1) was subject to sodium sulfate fractionation (18% saturation), and was allowed to pass through DEAE-cellulose (DE-52; Whattman) equilibrated with 17.5 mM phosphate buffer (pH6.3). A non-adsorption fraction was collected to obtain an anti-hGH rabbit polyclonal antibody IgG fraction.

(3) Preparation of the anti-hGH labeled antibody

The anti-hGH rabbit polyclonal antibody IgG fraction obtained in the above (2) was dialyzed with 0.1 M citrate buffer (pH 4.5) containing 0.1 M sodium chloride, pH was adjusted to 3.7 with 1N hydrochloric acid, 3% pepsin was added to the anti-hGH rabbit polyclonal antibody IgG fraction, and it was digested at 37° C. for 3.5 hours. The reaction was quenched by adjusting pH to 7.5 to 8.0 with 1M Tris solution. The mixture was gel-filtrated with S-200SF column (Pharmacia) equilibrated with 0.05 M phosphate buffer (pH 6.5) containing 2 mM disodium ethylenediamine tetraacetate and 0.1 M sodium chloride, and a fraction corresponding to an initially-eluted peak was collected.

To the collected fraction was added 1/50 amount of 0.2 M 2-mercaptoethylamine solution, and the mixture was reacted at 37° C. for 90 minutes. Then, the mixture was gel-filtrated with Sephadex G-25 column (Pharmacia) equilibrated with 0.05 M phosphate buffer (pH 6.5) containing 2 mM disodium ethylenediamine tetraacetate and 0.1 M sodium chloride, and a fraction corresponding to an initially-eluted peak was collected (Fab' fraction).

Separately, 5 mg of horse-radish derived peroxidase (TOYOBO Co., Ltd.; referred to as "POD") was dissolved in 0.1 M phosphate buffer (pH 7.0). To the mixture was added 4.0 mg of N-succinimidyl-4-(maleimidomethyl)-cyclohexane-1-carboxylate in 50 μL of dimethylformamide, and the mixture was kept at 30° C. for 60 min. The mixture was gel-filtrated with Sephadex G-25 column (Pharmacia) equilibrated with 0.05 M phosphate buffer (pH 6.5) containing 2 mM disodium ethylenediamine tetraacetate and 0.1 M sodium chloride, and a fraction corresponding to an initially-eluted peak was collected (pyridyldithio group-coupled POD fraction).

To the above Fab' fraction was added an equimolar amount of the pyridylthio group-coupled POD fraction, and the mixture was left at 4° C. overnight. The mixture was gel-filtrated with S-20OSF column equilibrated with 0.1 M phosphate buffer (pH 6.5) containing 0.1 M sodium chloride, and a fraction corresponding to an initially-eluted peak was collected (POD-labeled anti-hGH Fab' fraction). The fraction was treated with bovine serum albumin as a stabilizer at a level of 0.1%, and stored at 4° C. until use.

Example 2
Antigen specificity of the MTC6A monoclonal antibody

The MTC6A monoclonal antibody obtained according to Example 1 was evaluated by an immunoassay for its antigen specificity. The antigens used were purified 20 k hGH produced by gene recombination (JP-A 6-269292), and its analogous peptide hormones, human prolactin (referred to as "hPRL"; UCB BIOPRODUCTS) and human cilium somatomamotropin (referred to as "hCS"; CHEMICON). Each antigen was solidified on a 96-well microplate (Greiner) at an appropriate concentration (0 to 5000 ng/mL), and was then reacted with a solution of the MTC6A monoclonal antibody for evaluation. As a result, the MTC6A monoclonal antibody of this invention did not reacted with hPRL or hCS, analogous peptide hormones of hGH. The results are summarized in Table 1.

TABLE 1

Antigen specificity of the MTC6A monoclonal antibody

| Antigen | Reactivity |
|---------|------------|
| 20k hGH | + |
| hPRL | − |
| hCS | − |

+: reactive
−: nonreactive

Example 3
Reactivity of the MTC6A monoclonal antibody to 20 k hGH and 22 k hGH in a sandwich immunoassay The MTC6A monoclonal antibody obtained according to Example 1 was evaluated for its reactivity to 20 k hGH and 22 k hGH. The MTC6A monoclonal antibody was diluted with PBS to 10 μg/mL, aliquots (50 μL) of the solution were poured to a 96-well microplate (Greiner), and the microplate was left at 4° C. overnight. This plate was washed with washings (10 mM Tris-HCl buffer (pH: 8.0) containing 0.05% Tween 20), and treated with blocking solution 2 (4-fold dilution of Block Ace (Yukijirushi) in PBS) for blocking. After blocking solution 2 was removed, to 48 of 96 wells and the other 48 wells were added aliquots (100 μL) of 20 k hGH with an appropriate concentration (0 to 2 ng/mL) in blocking solution 2 and aliquots (100 μL) of 22 k hGH (Genotropin; Sumitomo Pharm.) with an appropriate concentration (0 to 30 ng/mL) in blocking solution 2, respectively, and then shaken at room temperature for 2 hours. After washing the plate with above mentioned washings, to the wells were added aliquots (100 μL) of 500-fold dilution of the POD-labeled anti-hGH antibody Fab' fraction of Referential Example 1 in an antibody diluent (10-fold dilution of Block Ace (Yukijirushi) in PBS), and then the microplate was shaken at room temperature for 2 hours. After washing, to the wells were added aliquots (50 μL) of a substrate solution (0.04% hydrogen peroxide containing 65 μg/mL of tetramethylbenzidin), and the plate was shaken at room temperature for 30 min. To the reaction solutions, aliquots (50 μL) of 1N sulfuric acid were added to quench the reaction, and absorbance at 450 nm was determined with Immunoreader (Nippon Intermed). The results are shown in FIG. 1. The MTC6A monoclonal antibody did not react with 22 k hGH even at 30 ng/mL which is higher than the normal blood level for 22 k hGH, but reacted with even at 10 pg/mL. Its cross-reactivity may be, therefore, estimated to be 0.03%.

Example 4
Determination of 20 k hGH in human blood with the MTC6A monoclonal antibody 20 k hGH in human blood was determined with the MTC6A monoclonal antibody. The MTC6A monoclonal antibody was diluted with PBS to 10 μg/mL, aliquots (50 μL) of the dilution were poured to a 96-well microplate (Greiner), and the plate was left at 4° C. overnight. After washing this plate with washings (10 mM Tris-HCl buffer (pH 8.0) containing 0.05% Tween 20), it was blocked with blocking solution 2 (4-fold dilution of Block Ace (Yukijirushi) with PBS). After removing blocking solution 2, to the plate were added aliquots (100 μL) of a test solution prepared by mixing human serum with blocking solution 2 or blocking solution 2 containing 500 or 1000 pg of standard 20 k hGH at ratio of 9:1, and the plate was shaken at room temperature for 2 hours. After washing with washings, to the plate were added aliquots (100 μL) of 500-fold dilution of the POD-labeled anti-hGH antibody Fab' fraction of Referential Example 1 in an antibody diluent (10-fold dilution of Block Ace (Yukijirushi) in PBS), and then the microplate was shaken at room temperature for 2 hours. After washing, to the plate were added aliquots (100 μL) of a substrate solution (0.1% citrate-phosphate buffer (pH 5.0) containing 0.67 mg/mL of 1,2-phenylenediamine(DAKO)), and the plate was shaken at room temperature for 30 min. To the reaction solutions, aliquots (100 μL) of 1N sulfuric acid were added to quench the reaction, and absorbance at 490 nm was determined with Immunoreader (Nippon Intermed), to determine the level of 20 k hGH by comparing with a calibration curve. The calibration curve had been developed by conducting determination as described above, using standard 20 k hGH diluted with blocking solution 2 instead of the above test solution. Table 2 shows the values of the calibration curve and coefficients of variation in determination, and Table 3 shows the measured values for the test solution and the recoveries of 20 k hGH added.

TABLE 2

Calibration curve for 20k hGH

| 20k hGH(pg/mL) | 0 | 10 | 100 | 500 | 1000 |
|---|---|---|---|---|---|
| Average of measured values ($A_{490}$) | 0.048 | 0.080 | 0.379 | 1.804 | 3.100 |
| Coefficient of variance (%) | 7.4 | 6.5 | 4.9 | 4.1 | 11.1 |

TABLE 3

Recovery of 20k hGH added

| | Amount of 20k hGH added | | |
|---|---|---|---|
| | 0 pg/mL | 50 pg/mL | 100 pg/mL |
| Serum 1 | | | |
| $A_{490}$ | 0.494 | 0.663 | 0.804 |
| Calculated value | 129 pg/mL | 177 pg/mL | 217 pg/mL |
| Recovery | 100% | 96% | 88% |
| Serum 2 | | | |
| $A_{490}$ | 1.522 | 1.681 | 1.856 |
| Calculated value | 421 pg/mL | 466 pg/mL | 516 pg/mL |
| Recovery | 100% | 90% | 95% |
| Serum 3 | | | |
| $A_{490}$ | 1.285 | 1.457 | 1.649 |
| Calculated value | 353 pg/mL | 402 pg/mL | 457 pg/mL |
| Recovery | 100% | 98% | 104% |

What is claimed is:

1. An immunoassay for detecting human growth hormone with a molecular weight of about 20,000 (20 k hGH) in an analyte comprising the following steps: (i) contacting an analyte suspected of comprising 20 k hGH with a monoclonal antibody that specifically binds to 20 k hGH, and detects 20 k hGH at a concentration of 10 pg/ml in said analyte and which monoclonal antibody is substantially non-reactive with human growth hormone having a molecular weight of about 22,000 (22 k hGH); and (ii) correlating the amount of 20 k hGH in said analyte based on the amount of immune complexes comprising 20 k hGH and said monoclonal antibody.

2. The immunoassay of claim 1, wherein said monoclonal antibody has a cross reactivity of 0.1% or less with 22 k hGH.

3. The immunoassay of claim 1, wherein said monoclonal antibody is attached to a label.

4. The immunoassay of claim 3, wherein said label is an enzyme and the immuno-assay is an enzyme immunoassay.

5. The immunoassay of claim 1 wherein said monoclonal antibody is produced by hybridoma FERM BP-5913.

6. The immunoassay of claim 1 wherein the analyte which is tested is selected from the group consisting of human blood, human urine, or samples comprising human blood or human urine.

7. A sandwich immunoassay for the detection of human growth hormone having a molecular weight of about 20,000 (20 k hGH) in an analyte comprising the following steps: (i) contacting an analyte suspected of containing 20 k hGH with a monoclonal antibody coupled to an insoluble carrier, wherein said monoclonal antibody specifically reacts to 20 k hGH, detects 20 k hGH at a concentration of 10 pg/ml in said analyte, and which is substantially non-reactive to 22,000 human growth hormone (22 k hGH) and which antibody is coupled to an insoluble carrier, to produce a conjugate in which 20 k hGH is specifically bound to said monoclonal antibody-insoluble carrier conjugate; (ii) reacting the conjugate obtained in step (i) with an anti-hGH enzyme-labeled antibody comprising an antibody which specifically binds to human growth hormone to produce a sandwich complex comprising anti-20 k hGH monoclonal antibody-20 k hGH-anti-hGH enzyme-labeled antibody comprised on the monoclonal antibody coupled insoluble carrier; and (iii) correlating the amount of 20 k hGH present in the analyte based on the activity of the enzyme used to label said anti-hGH antibody in step (ii).

8. The immunoassay of claim 7 wherein the analyte which is tested is selected from the group consisting of human blood, human urine or samples comprising human blood or human urine.

9. The method of claim 7 wherein said monoclonal antibody that specifically binds to 20 k hGH has a cross reactivity with 22 k hGH of 0.1% or less.

10. The method of claim 7 wherein said monoclonal antibody is produced by hybridoma FERM BP-5913.

\* \* \* \* \*